(12) United States Patent     (10) Patent No.:   US 12,629,128 B2

McLeod et al.     (45) Date of Patent:    May 19, 2026

(54) METHODS, PROCESSES, AND SYSTEMS FOR SOFT AND GLANDULAR TISSUE VASCULARITY ASSESSMENT

(71) Applicant: Morphometrix Imaging Technologies, Inc., George Town (KY)

(72) Inventors: Barry McLeod, Rocky View County (CA); Ali Meghoufel, Boucherville (CA)

(73) Assignee: Morphometrix Imaging Technologies, Inc., George Town (KY)

( * ) Notice: Subject to any disclaimer, the term of this patent is extended or adjusted under 35 U.S.C. 154(b) by 0 days.

(21) Appl. No.: 18/735,761

(22) Filed: Jun. 6, 2024

(65) Prior Publication Data

US 2024/0407751 A1     Dec. 12, 2024

Related U.S. Application Data

(60) Provisional application No. 63/471,440, filed on Jun. 6, 2023.

(51) Int. Cl.
    *A61B 8/08*       (2006.01)
    *A61B 8/00*       (2006.01)
    *G06T 5/30*       (2006.01)
    *G06T 5/70*       (2024.01)
         (Continued)

(52) U.S. Cl.
    CPC ............ *A61B 8/085* (2013.01); *A61B 8/0891* (2013.01); *A61B 8/469* (2013.01); *A61B 8/5269* (2013.01); *G06T 5/30* (2013.01); *G06T 5/70* (2024.01); *G06T 7/0012* (2013.01); *G06T 7/155* (2017.01); *G06T 2207/10132* (2013.01);

*G06T 2207/20036* (2013.01); *G06T 2207/20152* (2013.01); *G06T 2207/30101* (2013.01)

(58) Field of Classification Search
CPC ....... A61B 8/085; A61B 8/0891; A61B 8/469; A61B 8/5269; A61B 8/0825; A61B 8/5223; G06T 5/30; G06T 5/70; G06T 7/0012; G06T 7/155; G06T 2207/10132; G06T 2207/20036; G06T 2207/20152; G06T 2207/30101
See application file for complete search history.

(56) References Cited

U.S. PATENT DOCUMENTS

| | | | |
|---|---|---|---|
| 2014/0125691 A1* | 5/2014 | Lysyansky | A61B 8/486 345/672 |
| 2018/0103932 A1* | 4/2018 | Tahmasebi Maraghoosh | G16H 30/40 |
| 2023/0338537 A1* | 10/2023 | Oklu | A61P 31/00 |

FOREIGN PATENT DOCUMENTS

JP       H08190634 A   *   7/1996

* cited by examiner

*Primary Examiner* — Kaitlyn E Sebastian

(74) *Attorney, Agent, or Firm* — Tarter Krinsky & Drogin LLP

(57) ABSTRACT

The present technology relates to in vivo ultrasound imaging, and particularly to a proxy model of vascularity in soft and glandular tissue from two-dimensional ultrasound signals. The methods, processes, and systems herein are useful for detecting abnormal cell growth, and involve obtaining an ultrasound image of an anatomical structure of interest, isolating a region of interest (ROI) within the anatomical structure, identifying, within the ROI, one or more hyperechoic structures, subjecting the hyperechoic structures to (Continued)

2D and 3D smoothing, or 2D and 3D thinning, or 2D and 3D application of one or more morphological operations, to produce closed segmented structures.

5 Claims, 11 Drawing Sheets

(51) Int. Cl.
  *G06T  7/00*          (2017.01)
  *G06T  7/155*         (2017.01)

1

METHODS, PROCESSES, AND SYSTEMS FOR SOFT AND GLANDULAR TISSUE VASCULARITY ASSESSMENT

CROSS-REFERENCE TO RELATED APPLICATIONS

The present application claims the benefit of U.S. Provisional Application No. 63/471,440 filed Jun. 6, 2023, the entirety of which is incorporated by reference herein.

BACKGROUND

The present technology relates to methods, processes, and systems for assessing the vascularity of soft and glandular tissue during ultrasound imaging, and particularly to the creation of proxy models of vascularity in soft and glandular tissue from two-dimensional B-Mode ultrasound signals. As used herein, soft and glandular tissues include but are not limited to epithelial tissue, connective tissue, muscle tissue, and nerve tissue.

Ultrasound imaging is beginning to take a prominent place among the known imaging modalities in the detection of malignant tumor tissue. Previously, magnetic resonance imaging (MRI), computerized tomography scanning (CT-Scan), positron emission tomography scanning (PET Scan) and other nuclear imaging modalities were (and have continued to be) widely used by clinicians in oncology. In the last decade, the development of new high-performance ultrasound probes, as well as the emergence of ultrasound signal processing and segmentation methods, have facilitated and encouraged the use of ultrasound in the detection of high potential tumors.

A significant potential lies within the interactions of ultrasound waves with the malignant tumor tissues. An ongoing need exists for methods and processes that accurately display soft and glandular tissue, in a manner sufficient for a human reviewer to assess the likelihood of cancerous tissue.

SUMMARY

In certain embodiments, the present technology is directed to a method for detecting abnormal cell growth, the method comprising the steps of:

(a) obtaining an ultrasound image of an anatomical structure of interest, the anatomical structure including blood or lymphatic vessels that create liquid spaces in tissue;

(b) isolating a region of interest (ROI) within the anatomical structure;

(c) identifying, within the ROI, hyperechoic structures produced by an echo caused by coherent specular reflection at the liquid spaces in the tissue;

(d) enhancing the hyperechoic structures by subjecting them to: (i) 2D and 3D smoothing, (ii) 2D and 3D thinning, and (iii) 2D and 3D application of one or more of the following: morphological operations, erosion, dilation, closing pixels or watershed closing operations; to produce a segmented structure; and (e) analyzing the segmented structure by measuring the dimensions, quantity, density or number of segmented structures.

In certain embodiments, the ultrasound image in step (a) is a B-mode ultrasound cine loop scan.

In certain embodiments, step (c) is accomplished in one dimension by application of a thinning method as described in the following equation:

$$\begin{cases} u_i^{n+1} = u_i^n - \dfrac{\Delta t}{\Delta x}(\max(0, F_i) \cdot \Delta^+ u_i^n + \min(0, F_i) \cdot \Delta^- u_i^n) \\[2mm] F_i = F\left( \dfrac{u_{i+1}^{0,\sigma} - 2u_i^{0,\sigma} + u_{i-1}^{0,\sigma}}{\Delta x^2}, \dfrac{u_i^{0,\sigma} - u_{i-1}^{0,\sigma}}{\Delta x} \right) \\[2mm] \Delta^{\pm} u_i^n = \pm(u_{i\pm 1}^n - u_i^n) \end{cases} \quad (12)$$

to the shock function of the one-dimensional shock filter model as described in the following equation:

$$u_t = -F\left( (G_\sigma * u^0)_{xx}, (G_\sigma * u^0)_x \right)|\partial_x u| = 0 \text{ in } \mathbb{R} \times \mathbb{R}^+ \quad (11)$$

where the chosen shock function is described in the following equation:

$$F_i^2\left(u_{xx}^{0,\sigma}, u_u^{0,\sigma}\right) = \left(1 \times \text{sign}\left(u_x^{0,\sigma}\right)\right)_i = \text{sign}\left(u_x^{0,\sigma}\right)_i \quad (14)$$

where u denotes the one-dimensional (1D) signal of the B-Mode Ultrasound Scan image, $F^2$ is the shock function, $$u_{xx}^{0,\sigma} = \left(G_\sigma * u^0\right)_{xx}$$

is the second spatial derivative of the smoothed initial signal $u(x,t=0)=u^0$ at time zero, $$u_x^{0,\sigma} = \left(G_\sigma * u^0\right)_x$$

is the first spatial derivative of the smoothed initial signal $u(x,t=0)=u^0$ at time zero, $$u^{0,\sigma} = G_\sigma * u(x, t = 0)$$

is the initial signal $u(x,t=0)=u^0$ at time zero smoothed by a Gaussian smoothing operator $G_\sigma$ of standard deviation $\sigma$, the original signal is the curve signal described by $$u^{0,0} = \sin(x), \ x \in [0, 3\pi].$$

In certain methods, step (c) is further accomplished by application of a two-dimensional thinning method as described in the following two equations:

$$I_{i,j}^{n+1} = I_{i,j}^n - \Delta t \cdot R\left(I_{i,j}^n\right) \quad (16)$$

and $$\begin{cases} R(I^n_{i,j}) = \max(0, F^2_{i,j})\Delta^+_y(I^n_{i,j}) + \min(0, F^2_{i,j})\Delta^-_y(I^n_{i,j}) \\ F^2_{i,j} = \text{sign}(\nabla_y I^{\sigma,0})_{i,j} \\ \Delta^{\pm}_y I^n_{i,j} = \pm(I^n_{i,j\pm1} - I^n_{i,j}) \end{cases} \quad (17)$$

to the two-dimensional shock filter model:

$$\begin{cases} I_t + F\left((G_\sigma * I^0)_{\eta\eta}, (G_\sigma * I^0)_\eta\right)|I_n| = 0 \text{ in } R^2 \times R^+ \\ I(x, y, t = 0) = I^0(x) \end{cases} \quad (15)$$

where $$F^2_{i,j} = \text{sign}(\nabla_y I^{\sigma,0})_{i,j}$$

is the chosen two-dimensional (2D) shock function, $\nabla I$ is the gradient of I, the gradient direction is $\eta = \nabla I / \|\nabla I\|$, I denotes the two-dimensional (2D) signal of the B-mode Ultrasound Scan image, $I(x,y,t=0)=I^0$ is the initial signal in 2-two dimensional space at time zero, $G_\sigma$ is the Gaussian smoothing operator of standard deviation $\sigma$, $R^2 \times R^+$ denotes two dimensions in real space, $I^{0,\sigma} = G_\sigma * I^0$ is the smoothed initial signal in 2-two dimensional space at time zero.

In certain embodiments, abnormal cell growth is detected by identifying blood or lymphatic vessels. For example, a larger (or lower) number of blood vessels or lymphatic vessels than would normally be expected can be indicative of abnormal cell growth, which in turn can be indicative of a malignant tumor.

In certain embodiments, the present technology is directed to methods, processes, and systems related to the methods set forth herein.

BRIEF DESCRIPTION OF THE DRAWINGS

FIG. 1 and FIG. 2 illustrate angiogenesis: generation of blood vessels that supply tumors with nutrients to grow.

FIG. 3 shows piece-wise segmentation of a curved noise-free 1D signal.

FIG. 4 shows 1D shock deconvolution process of Equation (5) in certain embodiments herein, with various Gaussian smoothing kernels $\sigma$. Top row (from left): (a) original noise-free signal (sine wave); (b) noise-free signal restored by the shock filter; (c) original signal+white Gaussian noise defined with a SNR=10; bottom: noised signal restored using Gaussian deblurring (d) with $\sigma=1.5$, (e)$\sigma=3$, and (f)$\sigma=5$.

FIG. 5 shows a mosaic of images and their corresponding intensity profiles, as measured along the arrow seen in each frame, in certain embodiments herein. First row (from left): (a) original image, (b) speckle noised image (additive Gaussian noise with a SNR=10); second row: (c) Rudin shock enhancement, (d) Alvarez & Mazzora enhancement (k=0.3 and $\sigma=5$); third row: (e) Kornprobst et al. enhancement ($\alpha_d=0.6$, $\alpha_r=0.4$, $\tau=0.1$ and $\sigma=2$), (f) Coulon-Arridge enhancement ($\alpha=1$, k=10 and $\sigma=2$); fourth row: (g) Gilboa et al. enhancement ($\lambda1$ [r=0.7, $\theta=\pi/6$], $\lambda_2=0.3$ and a=0.3); and (h) Remaki and Cheriet enhancement ($\sigma=2$).

FIG. 6 shows changes in shock algorithm properties according to the sign of the shock function F in certain embodiments herein. Restorations after 30 iterations of the noise-free curved 1D signal ($u^{0,0}=\sin(x)$) by: (a) the classical 1D deconvolution shock algorithm, and (b) a 1D thinning shock algorithm according to an embodiment herein.

FIG. 7 shows: On left-hand panels, the solution using the classical deconvolution shock algorithm for the initial smoothed signal $u^{0,0}=\sin(5x)+\cos(7x)$. Discontinuities can be seen at the location of the zero-crossings of $$u^{0,0}_{xx}.$$

On right-hand panels, the solution is shown using a thinning shock algorithm of an embodiment herein applied on the same signal $u^{0,0}$. The thinning occurs at the location of the local maxima of $w_u^{0,0}$. (a): original signal; (b): signal sequence at iteration 8; and (c): signal sequence at iteration 30.

Figures 7, 8:
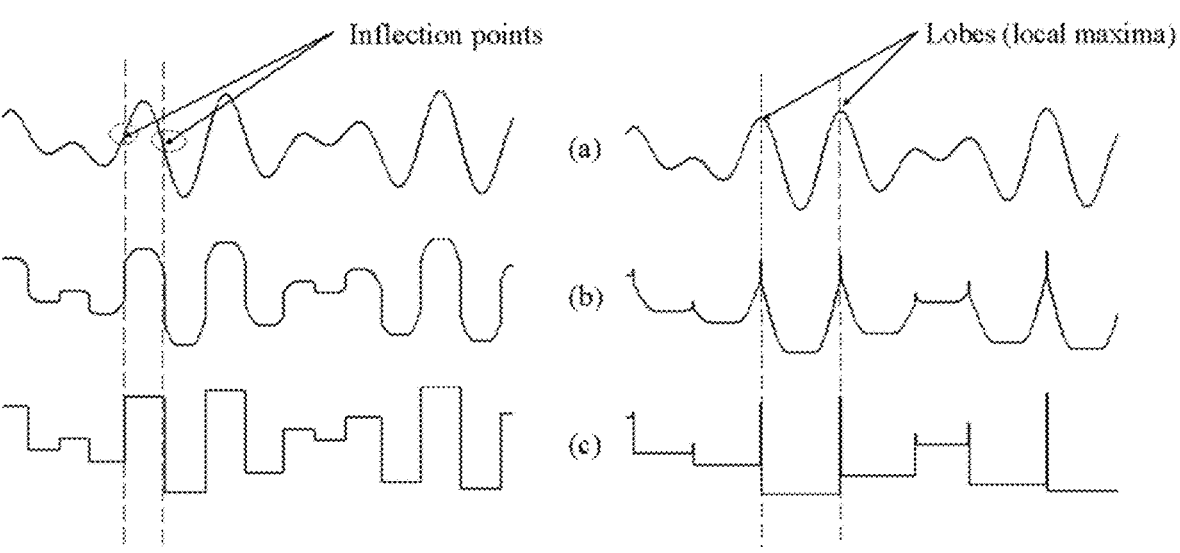

FIG. 8 is a two-dimensional image of an ultrasound of a female breast prior to processing by a tissue segmentation method described herein.

Figure 9:
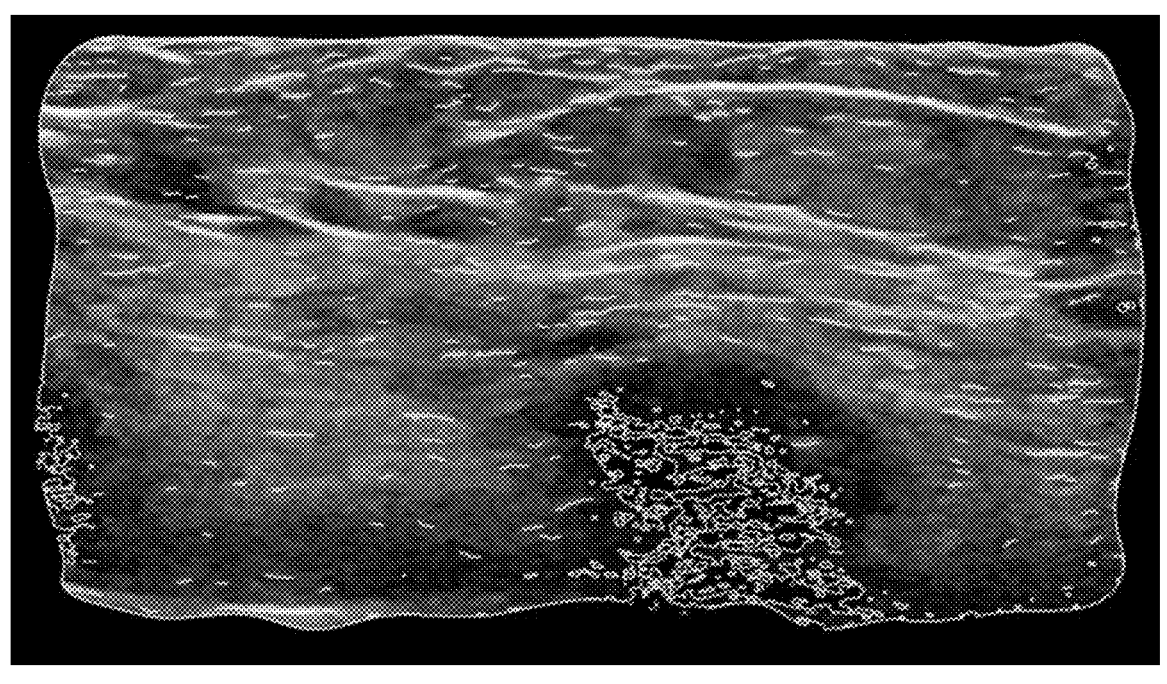

FIG. 9 is a two-dimensional image of an ultrasound of a female breast after processing by a tissue segmentation method described herein, and before application of morphological closing operators, overlain on a two-dimensional image of an ultrasound of a female breast prior to processing by a method herein, that identifies a highly vascularized malignant region.

Figure 10:
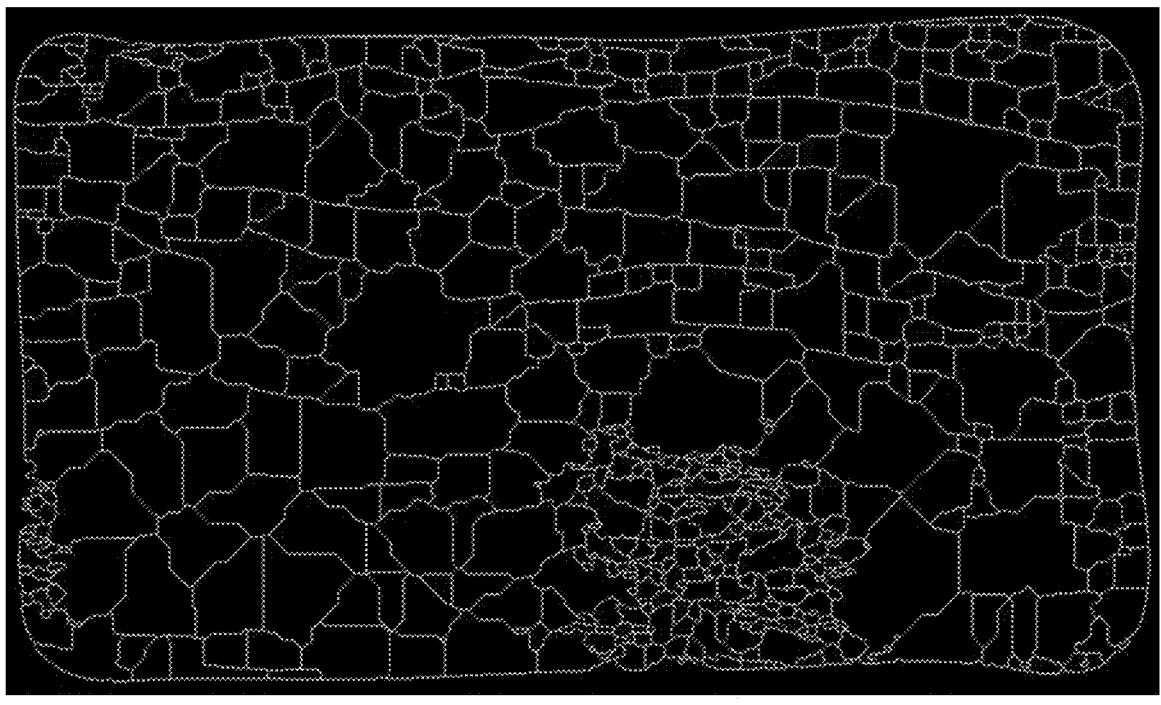

FIG. 10 is a two-dimensional image of an ultrasound of a female breast after processing by a tissue segmentation method described herein, after application of morphological closing operators to segment the tissue and quantify the tissue segment density.

Figure 11:
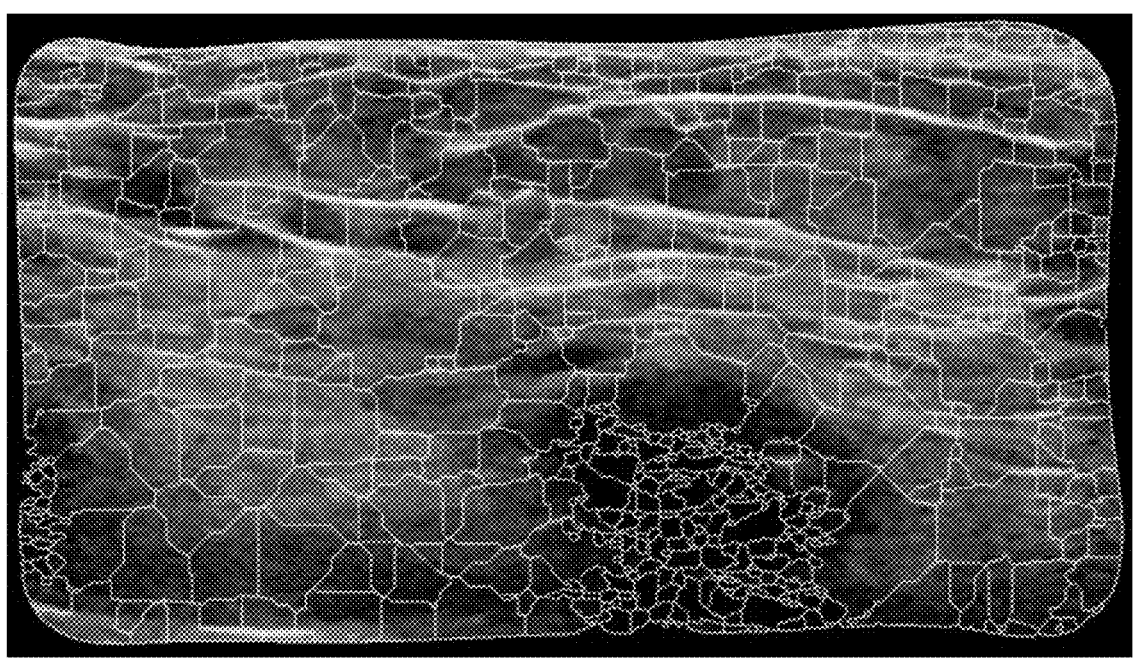

FIG. 11 is a two-dimensional image of an ultrasound of a female breast after processing by a tissue segmentation method described herein, after application of morphological closing operators to segment the tissue and quantify the tissue segment density, overlain on a two-dimensional image of an ultrasound of a female breast prior to processing by a method herein.

Figure 12:
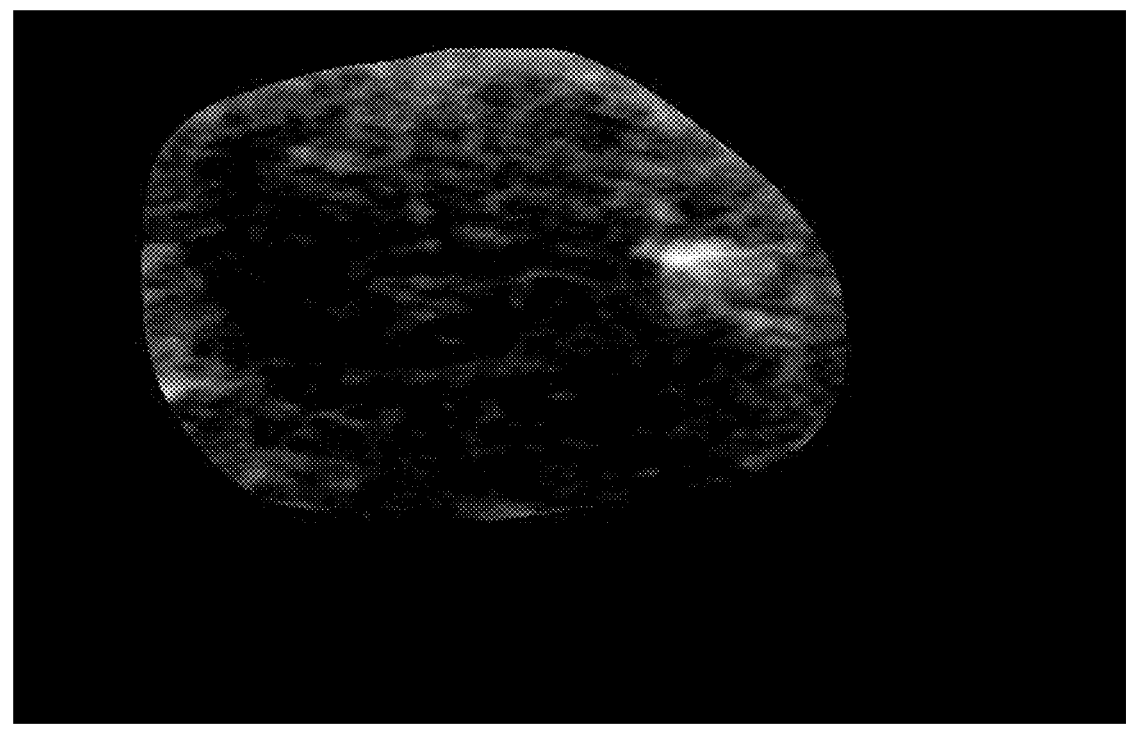

FIG. 12 is a two-dimensional image of an ultrasound of a malignant region of a female breast prior to processing by a tissue segmentation method described herein.

Figure 13:
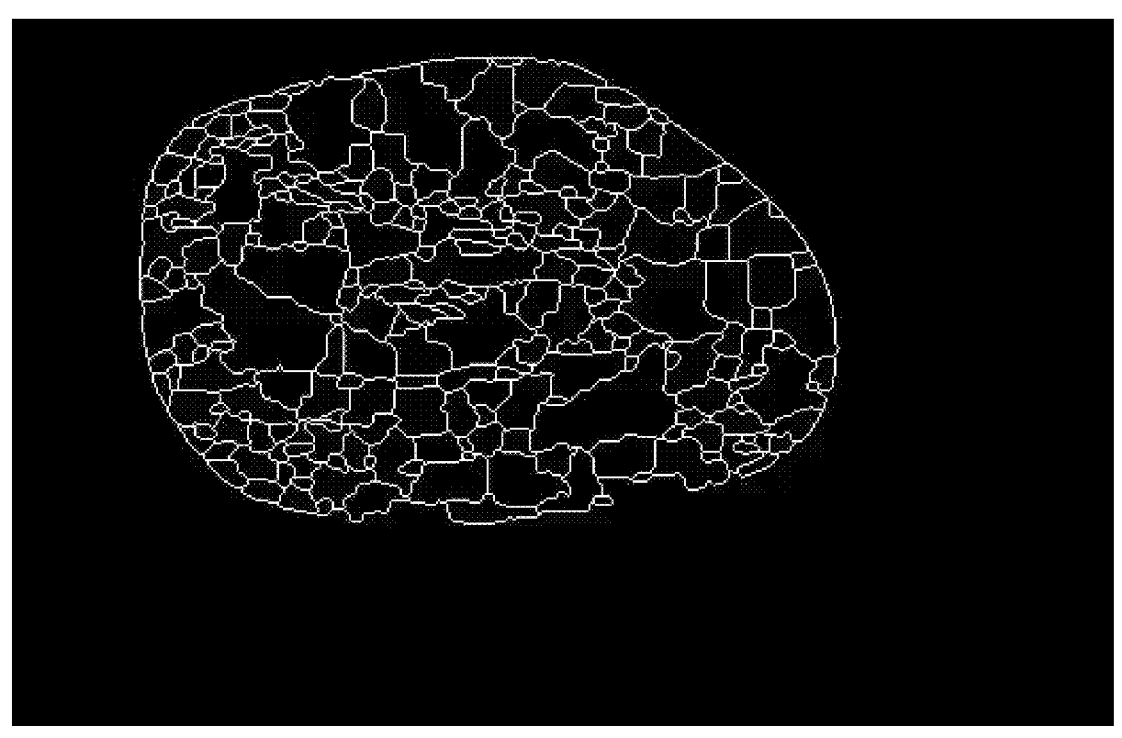

FIG. 13 is a two-dimensional image of an ultrasound a malignant region of a female breast after processing by a tissue segmentation method described herein, after application of morphological closing operations to segment the tissue and quantify the tissue segment density.

Figure 14:
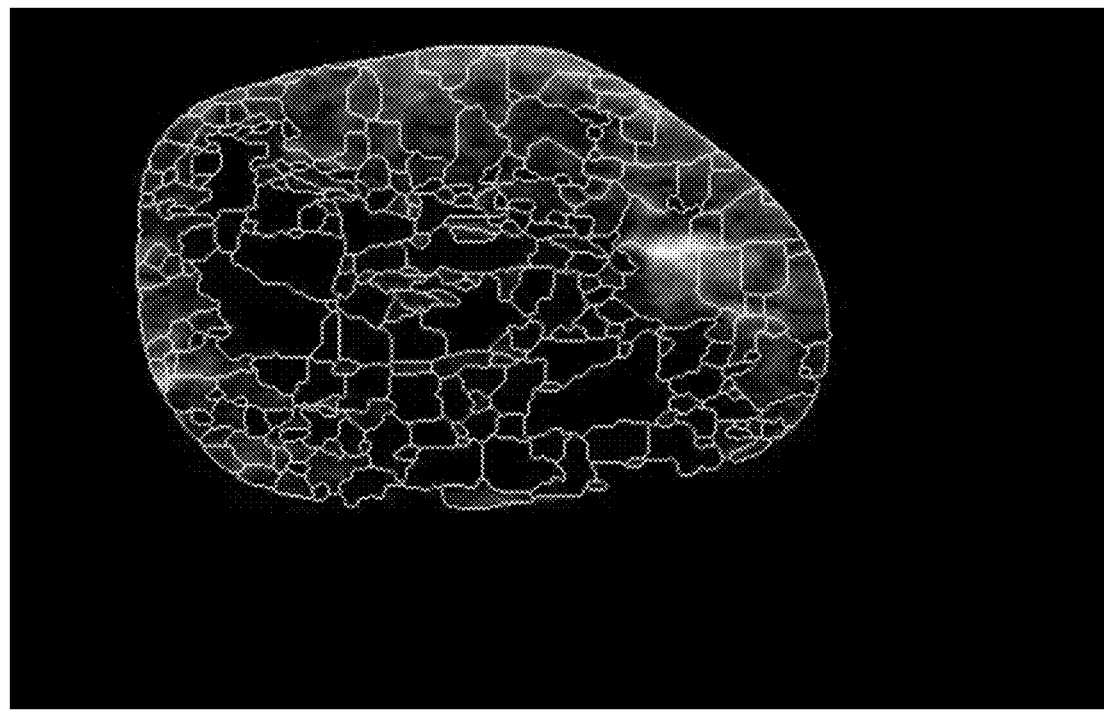

FIG. 14 is a two-dimensional image of an ultrasound of a malignant region of a female breast after processing by a tissue segmentation method described herein, after application of morphological closing operators to segment the tissue and quantify the tissue segment density, overlain on a two-dimensional image of an ultrasound of a malignant region of a female breast prior to processing by a method herein.

Figure 15:
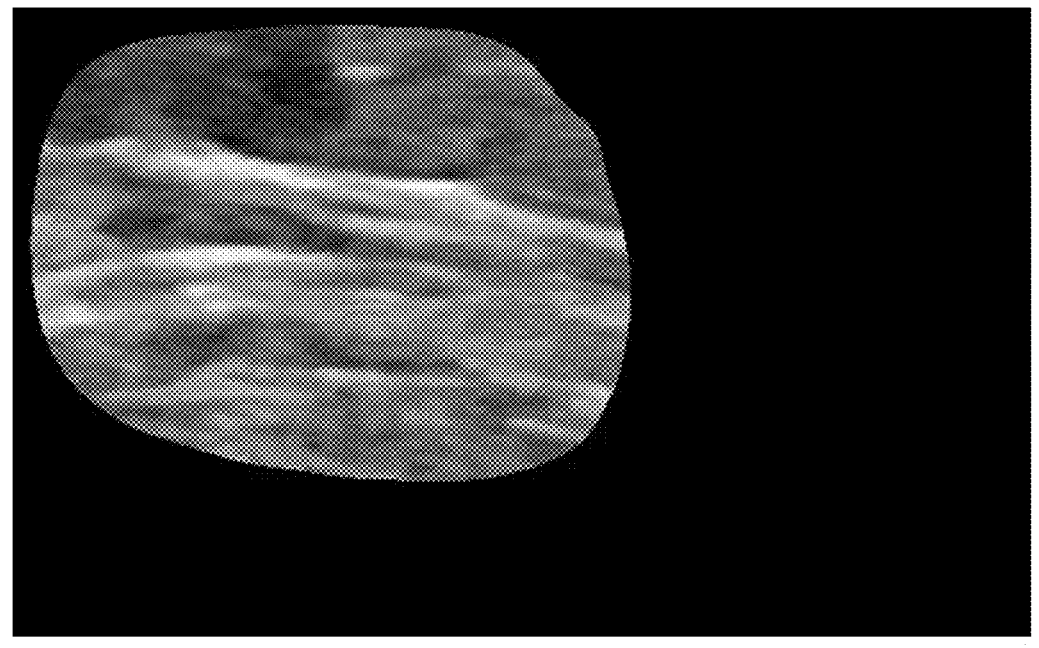

FIG. 15 is a two-dimensional image of an ultrasound of a nearby region of healthy tissue of a female breast prior to processing by a tissue segmentation method described herein to segment the tissue and quantify the tissue segment density.

Figure 16:
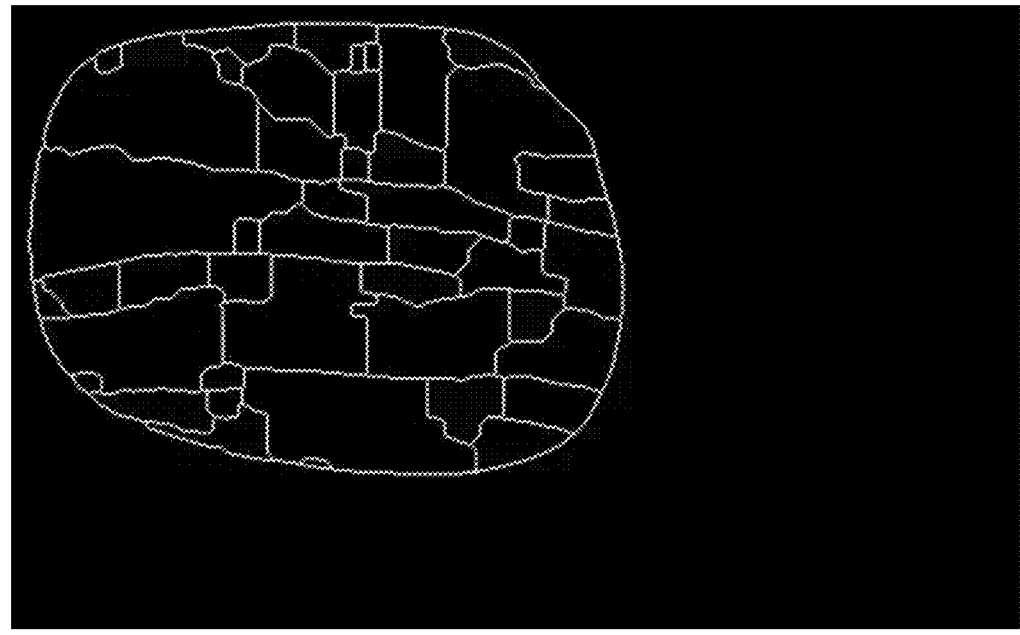

FIG. 16 is a two-dimensional image of an ultrasound of a nearby region of healthy tissue of a female breast after processing by a tissue segmentation method described herein after application of morphological closing operations to segment the tissue and quantify the tissue segment density.

Figure 17:
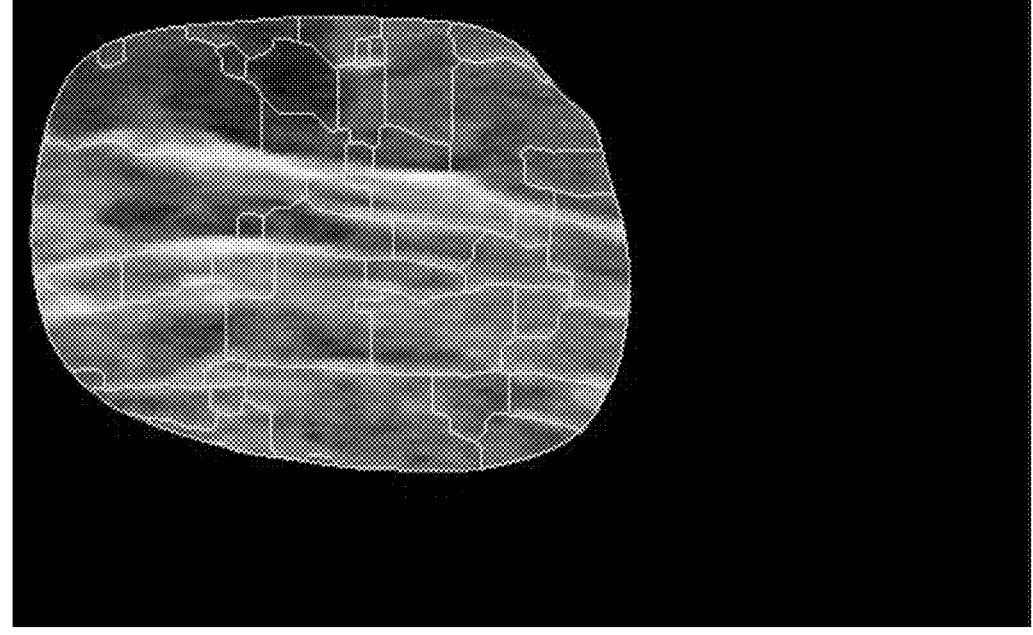

FIG. 17 is a two-dimensional image of an ultrasound of a nearby region of healthy tissue of a female breast after processing by a tissue segmentation method described herein after application of morphological closing operations to segment the tissue and quantify the tissue segment density, overlain on a two-dimensional image of an ultrasound of a nearby region of healthy tissue of a female breast prior to processing by a method herein to segment the tissue and quantify the tissue segment density.

Figure 18:
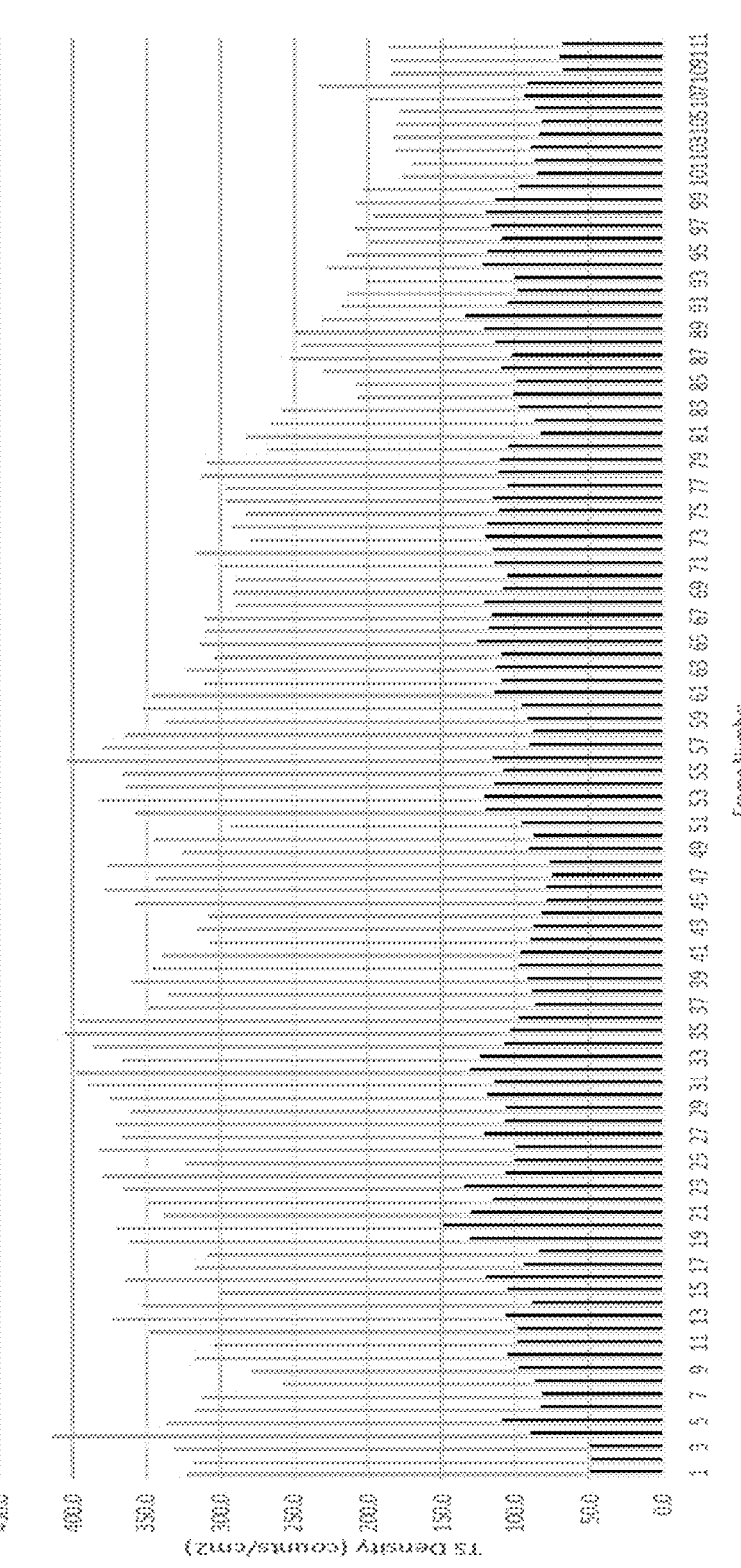

FIG. 18 is a graph of the comparison of the tissue segment density of a malignant region to that of a nearby healthy region in accordance with an embodiment of the technology herein.

DETAILED DESCRIPTION

All ingredient and formulation percentages are denoted in % w/w, unless explicitly noted in specific formulations. All ingredients are at 100% purity/concentration unless otherwise noted.

As used herein, "vascular" means relating to blood or lymphatic vessels. As used herein, "vascular network" means one or more blood or lymphatic vessels, and is not limited in number of blood or lymphatic vessels.

As used herein, "abnormal cell growth" means any cell growth that is greater or less than what is generally considered to be standard, and can be a factor indicative of a malignant tumor or cancer. As used herein, "malignant tumor," "cancer" or "cancerous" means a cluster of abnormal cells that is characteristic of a disease or disorder that exhibits the phenomenon of uncontrolled division of abnormal cells. Malignant tumors are in contrast to benign tumors, which exhibit slow cell growth rates, and exhibit much less vascularity than malignant tumors.

Throughout the present disclosure, when described in sequential words (for example, using "then" or "next"), such description is not limiting to the described steps in the particular order set forth, but also includes embodiments wherein the steps are presented in any order. Throughout the present disclosure, the use of the word "we" is not limited to a particular person or persons, but can indicate actions performed by any person or persons, or a computer, or artificial intelligence (A.I.)

In certain embodiments, the technology herein relates to methods, processes, and systems for assessing the vascularity of soft and glandular tissue during ultrasound imaging. As used herein, soft and glandular tissues include, for example, epithelial tissue, connective tissue, muscle tissue, and nerve tissue.

Epithelial tissue covers the surface of the body and lines the cavities and organs within. It is responsible for protection, absorption, and secretion. Examples include skin, mucous membranes, and the lining of the digestive tract.

Connective tissue provides support and connects different structures in the body. It includes a variety of tissues such as bone, cartilage, adipose (fat) tissue, and blood. Connective tissue is also important for storing energy, transporting nutrients and waste, and defending against infection.

Muscle tissue is responsible for movement and contraction of the body. There are three types of muscle tissue: skeletal, smooth, and cardiac. Skeletal muscle tissue is attached to bones and is responsible for voluntary movements, while smooth muscle tissue is found in organs and controls involuntary movements. Cardiac muscle tissue is found in the heart and is responsible for pumping blood throughout the body.

Nervous tissue includes specialized cells called neurons, which are responsible for transmitting and receiving signals throughout the body. Nervous tissue is found in the brain, spinal cord, and nerves, and is responsible for controlling and coordinating the functions of the body.

Figure 1:
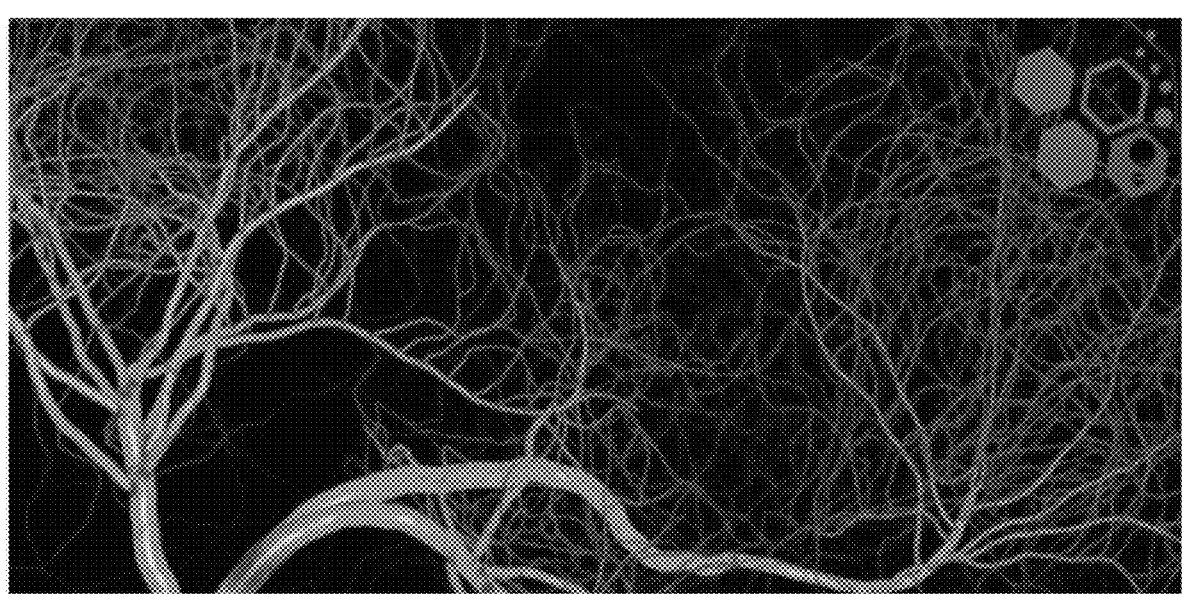
FIGS. 1 through 7 show various embodiments of the methods, processes, and systems herein.
Figure 2:
Figure 2:
Figure 2:
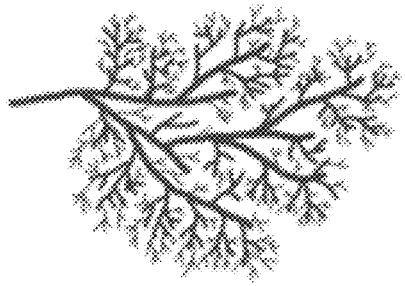

The formation of new blood vessels in organs can be a sign of metabolic activity that is highly correlated with the presence of a malignant tumor. Angiogenesis (see, e.g., FIGS. 1 and 2) is the growth and development of new blood vessels from existing vasculature in response to external chemical stimuli. One characteristic that allows a malignant cell to proliferate and form a tumor with a certain volume is its ability to elicit a response from the host, allowing it to obtain the nutrients it needs. The liquid spaces within living tissue created by blood and lymphatic vessels are highly reflective to the ultrasound wave propagation, and the coherent specular reflections appear as hyperechoic structures. However, their intensity is low, and they are noisy in the observed B-Mode Ultrasound images, making it impossible for radiographers and clinicians to detect or observer them. Furthermore, in malignant tumor tissue characteristics, necrosis is identified by its non-reflection of ultrasound. These characteristics are linked to the tumor cells that can form large colonies (e.g., several thousand cells). However, after a certain number of multiplications, the center of the colony (often made up of stem cells) no longer receives nutrients, becomes hypoxic and eventually dies. A central necrosis is characterized as anechoic structures on the observed B-Mode Ultrasound images and no significant signal can be found of this region.

The process of lymphangiogenesis involves the formation of new lymphatic vessels from pre-existing lymphatics. This can occur during embryonic development, wound healing and in various pathological contexts, including cancer. Lymphangiogenesis is considered a marker for dissemination, increased stage, and worse prognosis in certain cancers.

As used herein, the term "intense hyperechoic structures" refers to a cluster of such structures that is sufficiently significant as to be detected such that it can be determined that a region showing intense hyperechoic structures is within a region of interest (ROI). In various embodiments herein, a method, process, or system according to the present technology can identify intense hypoechoic structures within the ROI; or identifies all hypoechoic structures within the ROI, not just the intense hypoechoic structures. In the case of malignant tissue, a method, process, or system herein can, in certain embodiments, compare the region(s) of intense hypoechoic structures within the ROI to regions of contiguous or nearby healthy tissue (lower hypoechoic structure density) by processing the malignant region within the SROI (the secondary region of interest that contains the malignant tissue) and the TROI (tertiary region of interest—the healthy tissue region). In other embodiments, in the case of injuries to tendons, ligament, muscles and some other pathologies, a method, process, or system herein can identify the region(s) of low hypoechoic structure density within the ROI and compare them to regions of contiguous or nearby healthy tissue (regions of higher hypoechoic structure density) by processing the injured region within SROI (the secondary region of interest that contains the injured tissue) and the TROI (tertiary region of interest—the healthy tissue region).

As used herein the "region of interest" or "ROI" refers to the range of frames in a cine loop (video) that contains the anatomical structure or a portion of the structure that is of interest. The unnecessary frames can be edited out of the cine loop to create the ROI. For example, in taking a cine loop scan of a specific anatomical structure, the cine loop often contains frames of other anatomical structures or portions of the anatomical structure we are not interested in at the beginning or end of the cine loop or both; in such a case we can edit out the unnecessary frames to create the ROI. The cine loop also sometimes contains frames which are black with no signal at the beginning or end of the cine loop or both; in such a case we can edit out the unnecessary frames to create the ROI. In certain embodiments, we can then process the full frame of each frame in the ROI to identify a malignant or injured region. We can then edit out the unnecessary frames from the ROI (the frames that do not contain the malignant or injured region) to create the secondary region of interest (SROI) and then process the malignant or injured region within the frames of the SROI. In certain embodiments, we can then process a region of contiguous or nearby healthy tissue within the frames of the SROI to create a tertiary region of interest (TROI).

Based on clinicians' observations, in certain embodiments an ultrasound signal processing segmentation system has been developed, capable of detecting the coherent specular reflective signal of wave propagation at the liquid spaces. The system can be used to detect the signal, enhance it, and segment it to make the liquid spaces visible to clinicians. The methods, processes, and systems disclosed herein can, in certain embodiments, include applications of such technology in a manner that can enhance diagnosis and treatment of cancer, resulting in better patient outcomes.

Thus, in certain embodiments, the present technology relates to in vivo ultrasound imaging and in certain embodiments, including the creation of proxy models of vascularity in soft and glandular tissue from two-dimensional B-Mode Ultrasound Signals.

CT Scans, PET Scans, MRI and Ultrasound

A CT scan is an x-ray study that uses a computer to produce 3D cross-sectional images of the body. A CT scan cannot detect cancer, although it may be useful in helping to identify a mass and determine its location and size. A CT scan can also offer valuable information, such as its shape and possible makeup (e.g., solid versus liquid) that suggests that the mass could be cancerous. However, only a biopsy to obtain tissue, followed by pathology review of the tissue obtained under a microscope, can definitively determine cancer diagnosis.

A PET scan is a nuclear medicine imaging test that uses a form of radioactive sugar to create 3D color images to see how the body's cells are working. PET uses a radioactive material (e.g., radiopharmaceutical) made up of a radioactive isotope that is attached to a material used in the body, usually sugar (glucose). It travels through the body and gathers in cells that use a great deal of energy, such as cancer cells. The radioactive material gives off tiny positively charged particles (positrons). A camera records the interaction of the positrons with the tissue and turns the recording into computer images. PET scans detect areas of activity (including cell growth) in the body. More radioactive material collects in cancer cells than normal cells and will appear brighter on the image.

Magnetic Resonance Imaging (MRI), also known as magnetic resonance (MR) and nuclear magnetic resonance (NMR), is often used to detect cancer's presence and spread in the body. MRI can also assist physicians in planning cancer treatment, in much the same way as surgery or radiation. MRI creates cross-section "slices" of the interior of the subject's body from different angles, using magnets rather than radiation. An advantage of MRI is the ability to create images of soft tissues parts of the body that can be difficult to view using other types of imaging.

Ultrasound (also known as ultrasonography, sonography, or sonogram) is helpful for assisting healthcare professionals to detect tumors or areas of abnormal cell growth that do not show up on x-rays. Ultrasound is usually used to guide needles during biopsy of areas of interest. An advantage of ultrasound technology is that it does not require special preparation or highly invasive actions and can usually be done as an outpatient procedure.

The ultrasound apparatus creates images (sonograms) by giving off high-frequency sound waves that travel through the body, bouncing off organs and tissues and creating echoes. The apparatus turns the echoes into real-time computer images that show organ structure and movement, including even blood or lymph flow through vessels.

Advantages of ultrasound as a diagnostic tool include the following: ultrasound is particularly reliable at obtaining images of some soft tissue diseases that do not show up well on x-rays; it can be a useful way to discern fluid-filled cysts from solid tumors, as the different substances make different echo patterns. Ultrasound is also desirable for its ability to yield information relatively quickly (not requiring any special preparation or invasive steps), and does not expose the patient to radiation. However, ultrasound images are not generally as detailed as CT or MRI scans; cannot give information on whether a detected tumor is cancerous; and can be of limited usefulness in certain areas of the body, e.g., the lungs (because sound waves cannot travel through air) and bones.

Shock Filters Applied to Ultrasound Images

As used herein, "shock filter" means a nonlinear hyperbolic partial differential equation (PDE) filter regarded as a deconvolution filter, that is used to segment an image on piecewise constant segmentations.

Known shock filters rely on image deconvolution to create sharp discontinuities (the "shocks") between adjacent greyscale zones (influence zones) in the images and produce piecewise constant segmentations. The concept of image shock filter enhancement is adapted from nonlinear hyperbolic techniques. In the following equations, the u denotes the one-dimensional (1D) signal and the I denotes the two-dimensional (2D) signal of the B-Mode Ultrasound Scan image.

In the 1D case, the signal u(x,t) verifies the following hyperbolic equation:

$$u_t = a \cdot u_x \tag{1}$$

with the initial signal $u(x,t=0)=u^0$, and the scalar $a \geq 0$. $u_t$ and $u_x$ are the first derivatives in time and in space respectively. The solution of Equation (1) is $u(x,t)=u^0$ (x+at), and it corresponds to the initial signal propagated at speed −a.

In order to integrate signal deblurring and enhancement into the previous 1D model of Equation (1), it has been suggested to force the signal propagation speed to depend on the signal itself, and, more precisely on the sign of the second spatial derivative $u_{xx}$. This suggestion led Osher and Rudin to propose a one-dimensional (1D) model, which is written as follows:

$$u_t = -\text{sign}(u_{xx})|u_x| \qquad (2)$$

The model of Equation (2) can be interpreted as mathematical morphological operations. Indeed, according to the sign of the second derivative $u_{xx}$, Equation (2) can be decomposed into three parts, as follows:

$$u_t = \begin{cases} |u_x| & u_{xx} < 0 \\ -|u_x| & u_{xx} > 0 \\ 0 & u_{xx} = 0 \end{cases} \qquad (3)$$

Figure 3:
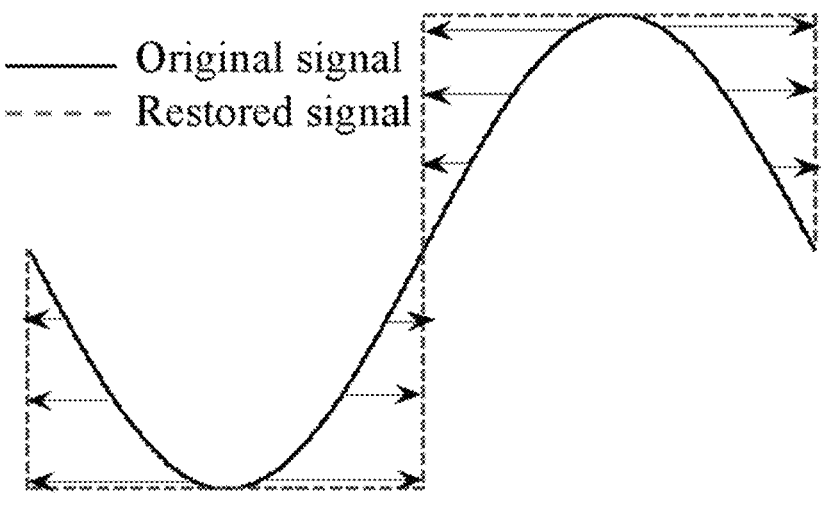

Shocks occur at signal inflection points (zero-crossings of $u_{xx}$) and lead to piece-wise constant solutions. As shown in FIG. 3, the shock process performs dilatation by solving $u_t=|u_x|$ in concave signal segments, whereas, in convex segments, measurement of the erosion that takes place is achieved by solving $u_t=-|u_x|$. The shock process maintains local extrema (maxima and minima) constant in time, without creating new ones.

The 2D shock filter model of Osher and Rudin has the following form:

$$I_t = -F(I_{\eta\eta})|\nabla I| \qquad (4)$$

with the initial condition (original image) $I(x,y,t=0)=I^0$, the gradient direction $\eta=\nabla I/\|\nabla I\|$, and the 2D shock function F, which must satisfy $F(0,0)=(0,0)$, and $(x,y)\times F(x,y)\geq 0$. $F(x,y)=(\text{sign}(x),\text{sign}(y))$ was chosen by Osher and Rudin to be the shock function in the case of Equation (4).

Osher and Rudin's shock filter model is very sensitive to noise: the second derivative amplifies noise, and so the location of the real zero-crossings of $u_{xx}$ in Equation (2) is a very difficult task. Several studies have addressed this issue, and various solutions have been suggested. Various others have opted to convolve the signal's second derivative with a smoothing Gaussian operator $G_\sigma$ of standard deviation $\sigma$ applied to the argument of the shock function of Equation (2):

$$u_t = -\text{sign}((G_\sigma * u)_{xx})|u_x| \qquad (5)$$

Figure 4:
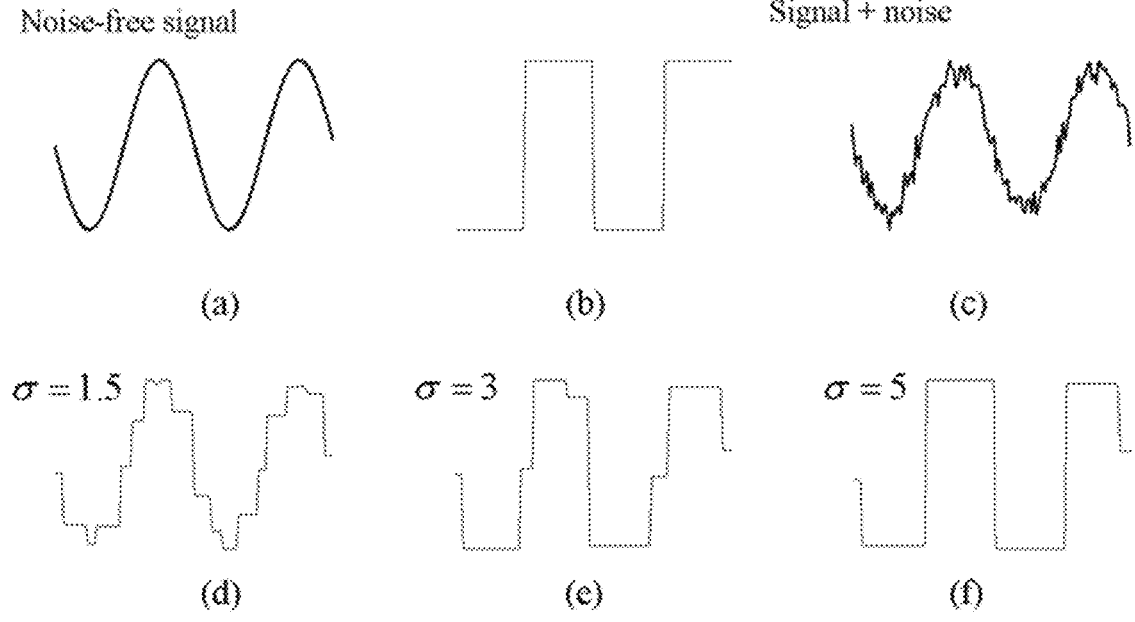

The Gaussian operator is not generally sufficient to overcome the noise problems. Indeed, the zero-crossings of $(G_\sigma*u)_{xx}$ depend on the width of the Gaussian support $[-\sigma, +\sigma]$. As shown in FIG. 4, the inflection points of the entity $(G_\sigma*u)_{xx}$ can change according to $\sigma$, which makes the identification of inflection points less accurate. Moreover, the effective parameter $\sigma$ is, in many cases, larger than the length of the signal, thus causing the signal boundary conditions to strongly affect the solution.

Alvarez and Mazzora proposed a new approach that combines enhancement and denoising: smoother signal sections are denoised, while edges are enhanced and sharpened. The main idea is to add an anisotropic diffusion term with an adaptive weight to the shock term. This model is written in 2D as follows:

$$I_t = k \cdot I_{\xi\xi} - \text{sign}(G_\sigma * I_{\eta\eta})|\nabla I| \qquad (6)$$

where the scalar $k \in [0,1]$, and $\xi$ is the perpendicular to the gradient direction $\eta$; i.e. $\xi=\eta^\perp$.

Thereafter, Komprobst et al. modified the previous equation to obtain:

$$I_t = \alpha_d(h_\tau I_{\eta\eta} + I_{\xi\xi}) - \alpha_r(1 - h_\tau)\text{sign}(G_\sigma * I_{\eta\eta})|\nabla I| \qquad (7)$$

where $h_\tau=h_\tau(|G_\sigma*\nabla I|)=1$ if $|G_\sigma*\nabla I|<\tau$ and $0$ otherwise. Parameters $\alpha_d$ and $\alpha_r$ are positive scalars. Isotropic diffusion occurs in homogeneous zones ($h_\tau=1$), whereas the Alvarez and Mazzora shock enhancement behavior occurs in non-homogeneous zones ($h_\tau=0$).

Using a different approach, Coulon and Arridge have proposed the following:

$$I_t = \text{div}(c(\nabla I)) - (1 - c(\nabla I))^\sigma \text{sign}(G_\sigma * I_{\eta\eta})|\nabla I| \qquad (8)$$

where $c(\nabla I)=\exp(-|\nabla I|^2/k)$. This filter has a similar behavior to the Kornprobst et al. model of Equation (7)—that is, isotropic diffusion in the homogeneous zones where the smoothed image gradient is low, while in zones where the gradient is high, the model behaves as Equation (5).

Gilboa et al. have proposed a model that relies on complex diffusion:

$$I_t = -\frac{2}{\pi}\arctan(a \cdot im(I/\theta))|\nabla I| + \lambda_1 I_{\eta\eta} + \lambda_2 I_{\xi\xi} \qquad (9)$$

where $\lambda_1$ is a complex number ($r$ and $\theta$ are its polar expressions), $\lambda_2$ is a scalar, $F(\bullet)=2/\pi\cdot\arctan(\bullet)$ is the shock function with its argument "a.im(I/$\theta$)", im being the imaginary part of the complex number and a is another scalar which controls the sharpness of the slope at the discontinuity-points.

Finally, Remaki and Cheriet have proposed a parametric shock filter to control shock positions, intensity, and propagation velocity. The 2D model is a combination in the x-y directions of the 1D model, as follows:

$$I_t = -a(G_\sigma * I^0) \cdot F((G_\sigma * I^0)_{\delta\delta}, (G_\sigma * I^0)_\delta) \cdot f_\delta(I) \qquad (10)$$

$$\delta = x, y \text{ directions}$$

In this equation, a, F, and $f$ are functions which control intensity, shock positions, and shock propagation velocity.

Figure 5:
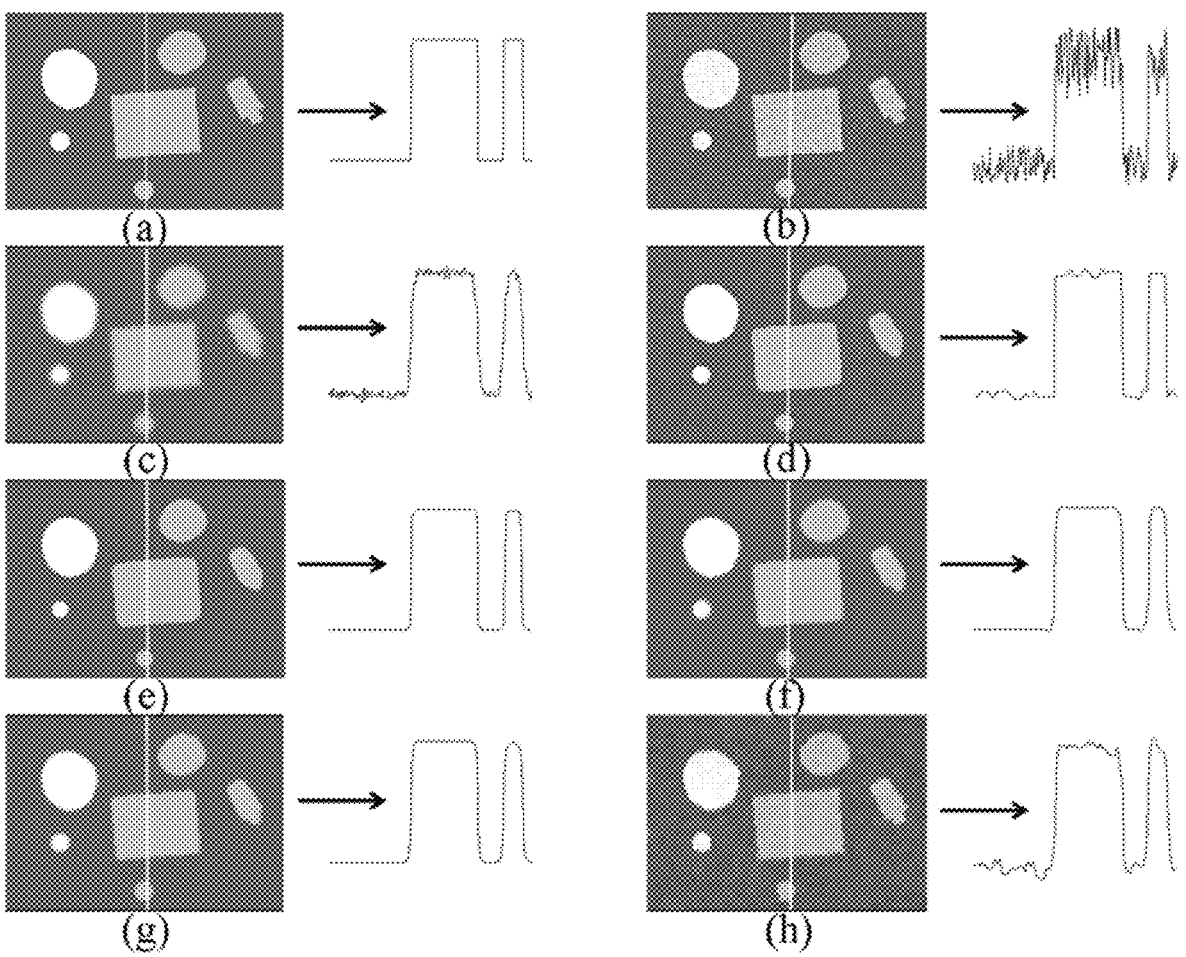

FIG. 5 shows a series of enhancements of a synthetic image (FIG. 5A) blurred and corrupted with noise (FIG. 5B). The results (image and intensity cross section profiles in panels c-h) are shown for the individual shock filters previously described. The image deconvolution changes from filter to filter. The Osher and Rudin shock filter (Equation 4, FIG. 5C) does not remove the blur because the detection of inflection points is almost impossible. Images enhanced by filters of Alvarez and Mazzora (Equation 6, FIG. 5D), Kornprobst et al. (Equation 7, FIG. 5E), and Coulon and Arridge (Equation 8, FIG. 5F), which all rely on Gaussian smoothing, are similar. The enhanced images obtained using the Gilboa et al. filter (Equation 9, FIG. 5G) are quite clear, even though no smoothing is used, but the sharpness of edges does not appear optimum. The Remaki and Cheriet results (Equation 10, FIG. 5H) are less accurate: sharp discontinuities are created in ox and oy directions (aniso-tropic along these two directions), and weak discontinuities are created in other directions of the plane. In conclusion, shock filters are very useful in the piecewise constant segmentations (deconvolution) process.

Methods

In certain embodiments, a method herein identifies liquid spaces within living tissue created by blood or lymphatic vessels. It can do any of the following: isolate the Region of Interest (ROI), identify the liquid spaces, and thin them to a very small width—e.g., the width of a single pixel, or of 3 to 7 pixels, of 5 pixels, or of 2 to 10 pixels. In certain embodiments, in addition to displaying a proxy of the vascular networks of tumors and other tissues, the method can produce a static analysis of the tissue segments associated with the vascular structure.

In various embodiments, a method, process or system herein can include any of the following steps (keeping in mind that in various embodiments, the steps need not be in the order presented below, but can be in any order):

Step 1. Acquisition of a B-Mode Ultrasound Cine Loop Scan of the anatomical structure of interest, transverse to its major, minor, or an oblique axis.

Step 2. Read, record, enter critical Cine Loop metadata: resolution, depth, size of frames, number of frames and the like. Record all metadata of Digital Imaging and Communications in Medicine (DICOM) format scans.

Step 3. Trim the Cine Loop to remove the excess frames and isolate the anatomical structure of interest.

Step 4. Isolate the region of interest (ROI) within the anatomical structure.

Step 5. Process the anatomical structure and ROI with a unique method herein to identify and enhance the intense hyperechoic structures produced by the echoes that are produced by coherent specular reflection at the liquid spaces created by blood or lymphatic vessels. Apply the following operations to the hyperechoic structures of the blood or lymphatic vessels to segment the tissue into structures:

2D/3D smoothing of hyperechoic structures;

2D/3D thinning of smoothed hyperechoic structures;

2D/3D application of morphological operations (erosion, dilation, closing pixels, and watershed operations).

Step 6. Statistical analysis of the segmented structures produced from the blood or lymphatic vessels, includ-ing one or more of the following:

Dimensions of structures

Density of Structures

Number of Structures

Regarding Step 5, in certain embodiments, a method herein is detailed as follows:

Genesis: Among segmentation methods in the literature that relate to the problem are variational methods and specifically shock filters. As discussed herein, a shock filter is a nonlinear hyperbolic partial differential equation (PDE)

filter regarded as a deconvolution filter used to segment an image on piecewise constant segmentations.

Inspired by the existing deconvolution shock filter meth-ods, an alternative approach is set forth in the various embodiments presented here. The alternative approach allows, in certain embodiments, the thinning (rather than the deconvolution) of the observed hyper-echoic structures cor-responding to the reflective signal of liquid spaces to facili-tate their extraction. Thus, a method herein can be based on the analytical shock filter form described by Alvarez and Mazzora, and on the numerical scheme developed in Remaki and Cheriet, adapted to handle B-scan images of tumors. Closing morphological operations can subsequently be applied to the enhanced images.

In certain embodiments, a thinning method herein is presented first analytically and numerically in the 1D case to clarify its behavior and to compare it with the classical deconvolution method; the 2D method can thereafter be applied to the one or more ultrasound images; and the morphological operations can be used in the final step. That is, in certain embodiments, the proposed thinning method is presented first analytically and numerically in the 1D case to clarify its behavior and to compare it with the classical deconvolution method, then the 2D method is applied to ultrasound images. The morphological operations can be used in the final step. In certain embodiments, this order of steps can be varied.

Segmentation Method Comprising Thinning Method+Mor-phological Operator

In certain embodiments, a method, process or system herein comprises a segmentation method that comprises two steps: (1) a thinning method as described herein; and (2) one or more morphological operators. This method can be used to characterize the internal structures of the soft and glan-dular tissue by extracting the hyper-echoic structures observed in B-Mode Ultrasound images and their corre-sponding tissue liquid spaces. In certain embodiments, an analytical and numerical presentation of the proposed thin-ning method is introduced, followed by a detailed descrip-tion of morphological operations applied to the enhanced images. In certain embodiments, this order of steps can be varied.

To facilitate the understanding of the behavior of the 2D shock filter thinning method on images, its 1D representa-tion, which is easier to analyze analytically, is presented first.

A. One Dimensional Thinning Shock Method

In certain embodiments, the implementation of a method herein is inspired by the 1D shock filter model proposed by Alvarez and Mazzora, and by Remaki and Cheriet, and described as:

$$u_t = -F\left(\left(G_\sigma * u^0\right)_{xx}, \left(G_\sigma * u^0\right)_x\right)|\partial_x u| = 0 \text{ in } \mathsf{R} \times \mathsf{R}^+ \qquad (11)$$

where $$u^{0,\sigma} = G_\sigma * u(x, t = 0)$$

that is a prior smoothing of the original signal by a Gaussian operator, and the shock function $F(\bullet,\bullet)$ is defined as described in the following sections.

The numerical scheme of the above hyperbolic model (Equation (11)) is an explicit upwind, and is written as follows:

$$\begin{cases} u_i^{n+1} = u_i^n - \dfrac{\Delta t}{\Delta x}\left(\max(0, F_i)\cdot\Delta^+u_i^n + \min(0, F_i)\cdot\Delta^-u_i^n\right) \\ F_i = F\left(\dfrac{u_{i+1}^{0,\sigma} - 2u_i^{0,\sigma} + u_{i-1}^{0,\sigma}}{\Delta x^2}, \dfrac{u_i^{0,\sigma} - u_{i-1}^{0,\sigma}}{\Delta x}\right) \\ \Delta^\pm u_i^n = \pm\left(u_{i\pm1}^n - u_i^n\right) \end{cases} \tag{12}$$

The result features depend on the characteristics of the shock function F. In the following, we describe two implementations of F providing either the classical deconvolution operation or the proposed thinning of the signal.

i. The Shock Function of the Classical Deconvolution Method

For the classical case of deconvolution, in which sharp discontinuities are created at inflexion points (i.e., zero-crossings of $$u_{xx}^{0,\sigma}),$$

the function F that satisfies Equation (12) is chosen as follows:

$$F_i^1\left(u_{xx}^{0,\sigma}, u_x^{0,\sigma}\right) = \left(\text{sign}\left(u_{xx}^{0,\sigma}\right)\cdot\text{sign}\left(u_x^{0,\sigma}\right)\right)_i \tag{13}$$

Figure 6:
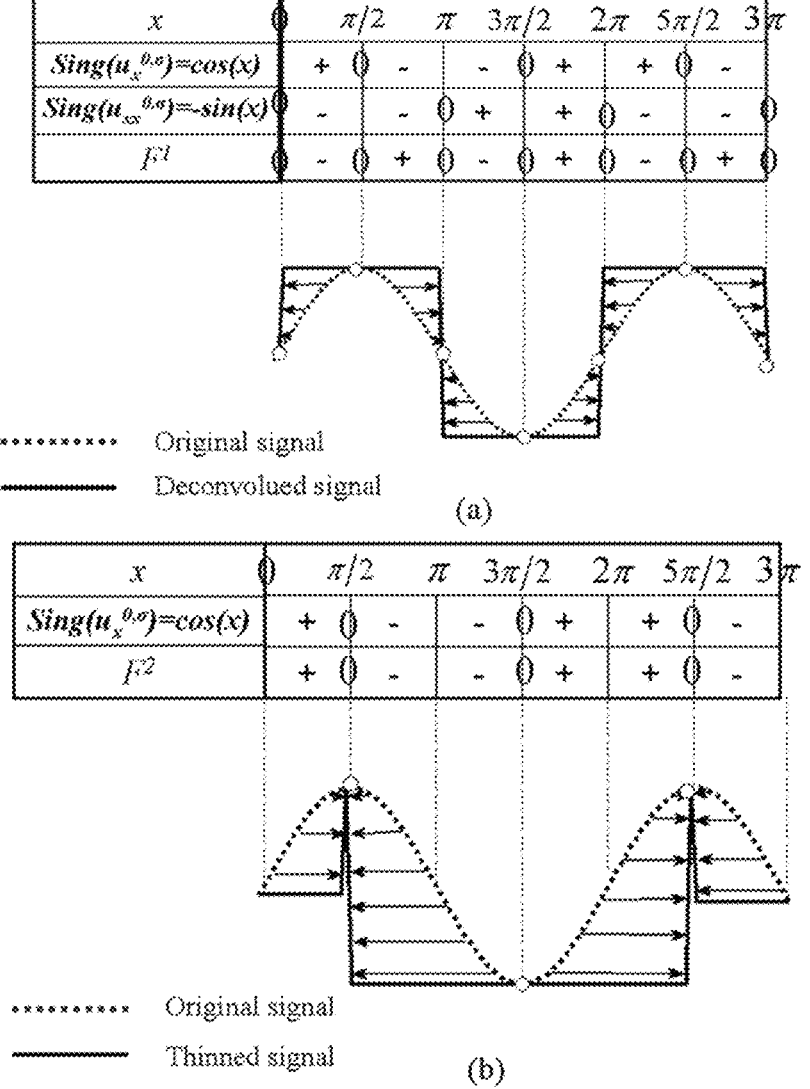

Here the superscript 1 is used to define the classical deconvolution process property. FIG. 6(*a*) is an example showing the evolution of the deconvolution process to create sharp discontinuities in the original signal (the curve signal described by $u^{0,0}=\sin(x)$, $x\in[0,3\pi]$) that evolves into a piecewise constant signal. The moving points of the original signal $u^{0,0}$ are governed by the sign of $F^1$. In the intervals] $\pi/2,\pi[U]3\pi/2,2\pi[U]5\pi/2,3\pi[$, $F^1$ is positive and signal points evolve by moving them to the right inducing the creation of jumps at $x=\pi^-,2\pi^-$ and $3\pi^-$, while $F^1$ is negative in the intervals] $0,\pi/2[U]\pi,3\pi/2[U]2\pi,5\pi/2[$ and signal points evolve by moving them to the left inducing the creation of jumps at $x=0^+$, $\pi^+$ and $2\pi^+$ ("−" and "+" indicate the left and right values of the central point). We notice that the sign of $F^1$ is null at points: $x=0,\pi/2,\pi,3\pi/2,2\pi,5\pi/2$ and $3\pi$ in which the signal remains invariant (extreme points).

ii. The Shock Function of the Original Thinning Method

Since one objective herein is to extract the hyper-echoic structures that are represented by local maxima of the intensity profile of the anatomical structure B-scan image, and inspired by the shock function properties of the classical deconvolution process $F^1$ described above, in certain embodiments the direction of movement of signal points can alternatively be controlled by introducing a new shock function that ensures an erosion process around those local maxima and a dilation elsewhere. The chosen shock function has the advantage of retaining local maxima and minima of the signal, while allowing signal points to move according to the sign of the shock function.

In certain embodiments herein, a shock function that can translate these analytical properties into the proposed thinning method, is Equation (14):

$$F_i^2\left(u_{xx}^{0,\sigma}, u_x^{0,\sigma}\right) = \left(1\times\text{sign}\left(u_x^{0,\sigma}\right)\right)_i = \text{sign}\left(u_x^{0,\sigma}\right)_i \tag{14}$$

In Equation (14) above, the superscript 2 is used here to describe the proposed thinning process property. FIG. 6(*b*) shows the behavior of this method and moving points of the original signal $u^{0,0}$ which are governed by the sign of the proposed function $F^2$. Around local maxima of the signal at $x=\pi/2$, $F^2$ is positive in the interval] $0,\pi/2[$ and signal points evolve to the right of the signal inducing the creation of jumps at $x=\pi/2^-$, while $F^2$ is negative in the interval] $\pi/2,3\pi/2$ [ and signal points evolve to the left of the signal inducing jumps at $x=\pi/2^+$. The sign of $F^2$ is null and the signal remains invariant at the central point $x=\pi/2$ (local maxima). This process can reflect erosion around $x=\pi/2$. The method can erode similarly the signal around the local maxima at $x=5\pi/2$.

Thus, in certain embodiments, the identification of, within the ROI, hyperechoic structures produced by an echo caused by coherent specular reflection at the liquid spaces in the tissue, can be accomplished in one dimension by application of a thinning method as described in the following equation:

$$\begin{cases} u_i^{n+1} = u_i^n - \dfrac{\Delta t}{\Delta x}\left(\max(0, F_i)\cdot\Delta^+u_i^n + \min(0, F_i)\cdot\Delta^-u_i^n\right) \\ F_i = F\left(\dfrac{u_{i+1}^{0,\sigma} - 2u_i^{0,\sigma} + u_{i-1}^{0,\sigma}}{\Delta x^2}, \dfrac{u_i^{0,\sigma} - u_{i-1}^{0,\sigma}}{\Delta x}\right) \\ \Delta^\pm u_i^n = \pm\left(u_{i\pm1}^n - u_i^n\right) \end{cases} \tag{12}$$

to the shock function of the one-dimensional shock filter model as described in the following equation:

$$u_t = -F\left(\left(G_\sigma * u^0\right)_{xx}, \left(G_\sigma * u^0\right)_x\right)|\partial_x u| = 0 \text{ in } \mathbb{R}\times\mathbb{R}^+ \tag{11}$$

where the chosen shock function is described in the following equation:

$$F_i^2\left(u_{xx}^{0,\sigma}, u_x^{0,\sigma}\right) = \left(1\times\text{sign}\left(u_x^{0,\sigma}\right)\right)_i = \text{sign}\left(u_x^{0,\sigma}\right)_i \tag{14}$$

where u denotes the one-dimensional (1D) signal of the B-Mode Ultrasound Scan image, $F^2$ is the shock function, $$u_{xx}^{o,\sigma} = \left(G_\sigma * u^0\right)_{xx}$$

is the second spatial derivative of the smoothed initial signal $u(x,t=0)=u^0$ at time zero, $$u_x^{o,\sigma} = \left(G_\sigma * u^0\right)_x$$

is the first spacial derivative of the smoothed initial signal $u(x,t=0)=u^0$ at time zero, $$u^{0,\sigma} = G_\sigma * u(x, t = 0)$$

is the initial signal u(x,t=0)=$u^0$ at time zero smoothed by a Gaussian smoothing operator $G_\sigma$ of standard deviation $\sigma$, the original signal is the curve signal described by $$u^{0,0} = \sin(x),$$

$$x \in [0, 3\pi].$$

FIG. 7 shows an embodiment with an application of the proposed thinning method versus the classical deconvolution method. The input is a 1D noise-free multimodal signal similar to intensity profiles of anatomical structure B-scan images after smoothing by $G_\sigma$. Local maxima mimic the hyper-echoic structures corresponding to the blood or lymphatic vessel spaces. The deconvolution method processes the signal by creating a sharp discontinuity that evolves into a piecewise constant signal, while the thinning method erodes the signal around local maxima.

The thinned process can be a more practical application than those known before, because, among other reasons, it can thin hyper-echoic structures when applied on soft or glandular tissue B-Mode Ultrasound images (as shown later); and it can pre-process them to facilitate their extraction using complementary morphological operations. Both methods are based on a stopping criterion on the error between two consecutive signal sequences, with a maximum of, in certain embodiments, 20 iterations, 30 iterations, 50 iterations, 80 iterations or 100 iterations.

B. Two-Dimensional Thinning Shock Method

In certain embodiments, a 2D thinning method herein is based on at least some of the same analytical properties as in 1D, and can be described by the following model:

$$\begin{cases} I_t + F\left((G_\sigma * I^0)_{\eta\eta}, (G_\sigma * I^0)_\eta\right)|I_\eta| = 0 \text{ in } R^2 \times R^+ \\ I(x, y, t = 0) = I^0(x) \end{cases} \quad (15)$$

As in the 1D case, in certain embodiments, the notation $I^{0,\sigma}=G_\sigma * I^0$ can be used for the smoothed initial image. The shock function is not easy to generalize from the 1D model, however, in certain embodiments, it can be estimated using the structural information contained in such images. Indeed, it has been found that parallel, and linear hyper-echoic structures are formed when the US wave propagation axis is perpendicular to the blood or lymphatic vessel spaces; in such condition, the gradient vector $\eta$ is parallel to that axis ($\eta$ is obviously perpendicular to the hyperechoic structures). Therefore, in certain embodiments it can be assumed that the $\eta$ is simply the y directional derivative of the image (y is the direction of the scan axis: major, minor, or oblique axis of the anatomical structure; x is perpendicular to the direction of the scan axis). The shock function $F^2$ plays the same role in 2D as in the 1D case, and it is written $$F_{i,j}^2 = \text{sign}\left(\nabla_y I^{\sigma,0}\right)_{i,j}.$$

The sign of each column of the matrix $F^2$ can be treated as a 1D signal.

In such case, the thinning method can then become:

$$I_{i,j}^{n+1} = I_{i,j}^n - \Delta t \cdot R(I_{i,j}^n) \quad (16)$$

where:

$$\begin{cases} R(I_{i,j}^n) = \max(0, F_{i,j}^2)\Delta_y^+(I_{i,j}^n) + \min(0, F_{i,j}^2)\Delta_y^-(I_{i,j}^n) \\ F_{i,j}^2 = \text{sign}(\nabla_y I^{\sigma,0})_{i,j} \\ \Delta_y^\pm I_{i,j}^n = \pm(I_{i,j\pm 1}^n - I_{i,j}^n) \end{cases} \quad (17)$$

Complementary Morphological Closing Operations

In certain embodiments, the segmentation of enhanced B-Mode Ultrasound images by 2D mathematical morphological operations can be performed to facilitate the extraction of quantitative data on tissue segments, and also to improve the 2D or 3D visualization of the anatomical internal structures. The mathematical morphological operations can proceed as follows for each enhanced image:

i. Background subtraction using the structuring element "rolling ball" with a radius of 5 pixels;

Closing Watershed operation method based on binary thickenings with a structuring element of 4 connected pixels. The Watershed operation can be used to overcome the absence of visible blood and lymphatic vessel structures parallel to the ultrasound beam on B-Mode Ultrasound images.

Reference is made to additional FIG. 8 through FIG. 17, which illustrate further embodiments herein.

In certain embodiments, a method, process or system herein is directed to an in vivo method for producing proxy models for vascularity of soft and glandular tissue. The method can be used with healthy, diseased, injured, and malignant tissue. Other embodiments include use for imaging various human and animal tissues, including but not limited to: prostate, breast, bladder, penis, ovaries, kidneys, pancreas, tendons, ligaments, and muscles.

In certain embodiments, 2D Ultrasound images can be obtained as one or more Cine Loops and processed by a method herein. In certain embodiments, the Cine Loop can be obtained in vivo from a female breast in freehand or automatically controlled mode scanning.

In certain embodiments, a Cine Loop obtained herein can be trimmed as necessary to remove any non-relevant 2D images. The anatomical structure of interest, a Region of Interest (ROI) or a Primary Region of Interest (PROI), can be isolated in one or more remaining images, and such images can be processed by a method in any embodiment herein.

In certain embodiments, for example, as shown in FIG. 9, a suspected malignant region, such as a lesion, can be identified in an image that displays it.

In certain embodiments, once a suspected malignant region is identified within an image, the Cine Loop can again be trimmed to remove the frames that do not display the lesion, the secondary region interest (SROI). The lesion within the SROI can then be isolated in any one or more remaining images and the Cine Loop can then be processed by a method herein. In certain embodiments, the method can determine the average tissue segment density of the suspected malignant region as a proxy for vascularity of the region.

In certain embodiments, the trimmed Cine Loop containing only the images that display the suspected lesion can then be processed by the method after a contiguous or nearby region of healthy tissue, the tertiary region of interest (TROI), is isolated in the same frames as those of the SROI that were processed by the method. In certain embodiments, the method can determine the average tissue segment density of the contiguous or nearby healthy region as a proxy for vascularity of the contiguous or healthy region.

In certain embodiments, the tissue segment density of the lesion region, the suspected malignant region, can be compared to the tissue segment density of the contiguous or nearby healthy region as a proxy for relative vascularity by a variety of analytical and visual techniques. In certain embodiments, the tissue segment densities of the two regions can be compared and displayed graphically—for example, as shown in FIG. 18.

In certain embodiments, a method, process or system herein can be applied to a tendon, ligament, or muscle as a proxy for the severity of an injury or the extent of pathology or disease. In the cases of tendons, ligaments, and muscles, the lesion region can be the suspected injury or pathological region; and the tissue segment density can be the fiber bundle density.

In certain embodiments, a method, process or system herein can be applied to any other pathology or disease, including but not limited to: a benign tumor, tissue atrophy, tissue hypertrophy (e.g., bladder wall thickening) as a proxy for the severity of the pathology or disease.

FIGS. 8, 12, and 15 show displays of isolated 2-D ultrasound images of living breast tissue prior to processing by a method herein, as can be generated in various embodiments herein.

FIGS. 10, 13, and 16 show displays of isolated 2-D ultrasound images of segmented living breast tissue after processing by a method herein that visualizes the tissue segments, as can be generated in various embodiments herein.

FIGS. 11, 14, and 17 show displays of isolated 2-D ultrasound images of segmented living breast tissue after processing by a method herein, overlain on unsegmented images prior to processing by the method, as can be generated in various embodiments herein.

FIG. 18 shows a graphical comparison of tissue density as a proxy for vascularity of malignant and nearby healthy living breast tissue, as determined by application of a method herein to B-Mode Ultrasound images of the tissue, as can be generated in various embodiments herein.

Although the present technology has been described in relation to embodiments thereof, these embodiments and examples are merely exemplary and not intended to be limiting. Many other variations and modifications and other uses will become apparent to those skilled in the art. The present technology should, therefore, not be limited by the specific disclosure herein, and can be embodied in other forms not explicitly described here, without departing from the spirit thereof. The term "or" as used herein means any one or more of the alternatives, including all of the alternatives.

We claim:

1. A method for detecting abnormal cell growth, the method comprising the steps of:

(a) obtaining an ultrasound image of an anatomical structure of interest, the anatomical structure including blood or lymphatic vessels that create liquid spaces in tissue;

(b) isolating a region of interest (ROI) within the anatomical structure;

(c) identifying and enhancing, within the ROI, hyperechoic structures produced by an echo caused by coherent specular reflection at the liquid spaces in the tissue by subjecting a radio frequency signal generated from the echo to: (i) 2D and 3D smoothing, (ii) 2D and 3D thinning, and (iii) 2D and 3D application of one or more of the following: morphological operations, erosion, dilation, closing pixels or watershed closing operations; to produce a segmented structure; and (d) analyzing the segmented structure by measuring dimensions, quantity, density or number of segmented structures.

2. The method of claim 1, wherein the ultrasound image in step (a) is a B-mode ultrasound cine loop scan.

3. The method of claim 1, wherein step (c) is accomplished in one dimension by application of a thinning method as described in the following equation:

$$\begin{cases} u_i^{n+1} = u_i^n - \frac{\Delta t}{\Delta x}(\max(0, F_i) \cdot \Delta^+ u_i^n + \min(0, F_i) \cdot \Delta^- u_i^n) \\ F_i = F\left(\frac{u_{i+1}^{0,\sigma} - 2u_i^{0,\sigma} + u_{i-1}^{0,\sigma}}{\Delta x^2}, \frac{u_i^{0,\sigma} - u_{i-1}^{0,\sigma}}{\Delta x}\right) \\ \Delta^{\pm} u_i^n = \pm(u_{i\pm 1}^n - u_i^n) \end{cases} \quad (12)$$

to a shock function of a one-dimensional shock filter model as described in the following equation:

$$u_t = -F\left(\left(G_\sigma * u^0\right)_{xx}\right), \quad (11)$$

$$\left(G_\sigma * u^0\right)_x)|\partial_x u| = 0 \text{ in } \mathbb{R} \times \mathbb{R}^+$$

where a chosen shock function is described in the following equation:

$$F_i^2\left(u_{xx}^{0,\sigma}, u_x^{0,\sigma}\right) = \left(1 \times \text{sign}\left(u_x^{0,\sigma}\right)\right)_i = \text{sign}\left(u_x^{0,\sigma}\right)_i \quad (14)$$

where u denotes a one-dimensional (1D) signal of a B-Mode Ultrasound Scan image, $F^2$ is the shock function, $$u_{xx}^{\rho,\sigma} = \left(G_\sigma * u^0\right)_{xx}$$

is a second spatial derivative of a smoothed initial signal $u(x,t=0)=u^0$ at time zero, $$u_x^{\rho,\sigma} = \left(G_\sigma * u^0\right)_x$$

is a first spatial derivative of the smoothed initial signal $u(x,t=0)=u^0$ at time zero, $$u^{0,\sigma} = G_\sigma * u(x, t = 0)$$

is an initial signal $u(x,t=0)=u^0$ at time zero smoothed by a Gaussian smoothing operator $G_\sigma$ of standard deviation $\sigma$, the original signal is a curve signal described by $$u^{0,0} = \sin(x),$$

$$x \in [0, 3\pi].$$

4. The method of claim 3, wherein step (c) is further accomplished by application of a two-dimensional thinning method as described in the following two equations:

$$I_{i,j}^{n+1} = I_{i,j}^n - \Delta t \cdot R(I_{i,j}^n)$$ (16)

and $$\begin{cases} R(I_{i,j}^n) = \max(0, F_{i,j}^2)\Delta_y^+(I_{i,j}^n) + \min(0, F_{i,j}^2)\Delta_y^-(I_{i,j}^n) \\ F_{i,j}^2 = \text{sign}(\nabla_y I^{\sigma,0})_{i,j} \\ \Delta_y^\pm I_{i,j}^n = \pm(I_{i,j\pm1}^n - I_{i,j}^n) \end{cases}$$ (17)

to a two-dimensional shock filter model:

$$\begin{cases} I_t + F\big((G_\sigma * I^0)_{\eta\eta}, (G_\sigma * I^0)_\eta\big)|I_\eta| = 0 \text{ in } R^2 \times R^+ \\ I(x, y, t = 0) = I^0(x) \end{cases}$$ (15)

where $$F_{i,j}^2 = \text{sign}(\nabla_y I^{\sigma,0})_{i,j}$$

is the chosen two-dimensional (2D) shock function, $\nabla I$ is the gradient of I, the gradient direction is $\eta = \nabla I / \|\nabla I\|$, I denotes the two-dimensional (2D) signal of a B-mode Ultrasound Scan image, $I(x,y,t=0) = I^0$ is the initial signal in 2-two dimensional space at time zero, $G_\sigma$ is the Gaussian smoothing operator of standard deviation $\sigma$, $R^2 \times R^+$ denotes two dimensions in real space, $I^{0,\sigma} = G_\sigma * I^0$ is the smoothed initial signal in 2-two dimensional space at time zero.

5. The method of claim 1, wherein the abnormal cell growth is detected by identifying blood or lymphatic vessels.

\* \* \* \* \*